(12) United States Patent
Sui et al.

(10) Patent No.: US 7,951,083 B2
(45) Date of Patent: May 31, 2011

(54) MOTION ANALYSIS IMPROVEMENTS FOR MEDICAL DIAGNOSTIC ULTRASOUND

(75) Inventors: Lei Sui, Newcastle, WA (US); Patrick Von Behren, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1518 days.

(21) Appl. No.: 11/051,224

(22) Filed: Feb. 4, 2005

(65) Prior Publication Data

US 2005/0203395 A1 Sep. 15, 2005

Related U.S. Application Data

(60) Provisional application No. 60/542,121, filed on Feb. 5, 2004.

(51) Int. Cl.
*A61B 8/00* (2006.01)
(52) U.S. Cl. ........................................................ 600/437
(58) Field of Classification Search .................. 600/437
See application file for complete search history.

(56) References Cited

U.S. PATENT DOCUMENTS

| | | | |
|---|---|---|---|
| 4,458,688 A | | 7/1984 | Von Behren |
| 5,213,105 A | * | 5/1993 | Gratton et al. ............. 600/473 |
| 5,235,984 A | * | 8/1993 | D'Sa ......................... 600/443 |
| 5,615,680 A | * | 4/1997 | Sano .......................... 600/437 |
| 5,638,820 A | | 6/1997 | Chen et al. |
| 5,805,135 A | * | 9/1998 | Suzuoki et al. ............ 345/420 |
| 5,850,474 A | * | 12/1998 | Fan et al. .................. 382/173 |
| 6,258,029 B1 | | 7/2001 | Guracar et al. |
| 6,331,851 B1 | * | 12/2001 | Suzuki et al. .............. 345/419 |
| 6,368,277 B1 | | 4/2002 | Mao et al. |
| 6,461,299 B1 | * | 10/2002 | Hossack ...................... 600/437 |
| 6,464,640 B1 | | 10/2002 | Guracar et al. |
| 6,527,717 B1 | * | 3/2003 | Jackson et al. ............. 600/437 |
| 6,558,324 B1 | | 5/2003 | Von Behren et al. |
| 6,626,836 B2 | | 9/2003 | Mao et al. |
| 6,718,055 B1 | * | 4/2004 | Suri ............................ 382/128 |
| 7,295,693 B2 | * | 11/2007 | Kaufman et al. .......... 382/131 |
| 2004/0015081 A1 | * | 1/2004 | Kramer et al. ............. 600/439 |
| 2004/0138567 A1 | * | 7/2004 | Ito et al. ..................... 600/458 |
| 2005/0033179 A1 | * | 2/2005 | Gardner et al. ............ 600/458 |
| 2005/0203395 A1 | | 9/2005 | Sui et al. |

OTHER PUBLICATIONS

"Echocardiographic Evaluation of Left Ventricular Wall Motion Using Still-Frame Functional Parametric Imaging," by Enrico G. Caiani et al.; University of Chicago, Illinois; Abstract: 1064-133; Citation Feb. 2001, vol. 37, No. 2, Supplement A; pp. 1A-648A; Echo Assessment of Regional and Global Function; Orange County Convention Center.

(Continued)

*Primary Examiner* — Tse Chen
*Assistant Examiner* — Hien Nguyen

(57) ABSTRACT

The phase or associated amplitude analysis of a sequence of images is improved by, first, providing quantifications in response to the phase or amplitude information. For example, a value or values representing asynchrony between different locations through a sequence of images may provide useful diagnostic information. Second, since heart motion or other motion within a body may become complex, multiple harmonics may be used in addition to the first harmonic or fundamental information for parametrically imaging a motion. Third, where different portions of a cycle have different characteristics, such as the systolic phase and diastolic phase of a heart cycle, images associated with each of the portions may be separated from other portions. A phase or amplitude analysis of the sequence of images for each portion is handled separately.

17 Claims, 2 Drawing Sheets

OTHER PUBLICATIONS

"Echocardiographic Phase Analysis: Timing of the Cardiac Cycle Using Left Atrial Motion," by Susheel K. Kodali et al.; University of California, San Francisco, San Francisco, CA; American College of Cardiology; Abstract; Control/Tracking No. 04-A-299907-ACC; printed on Sep. 17, 2003; 2 pgs.

"Ventricular Synchrony As Determined by Phase Analysis Correlates with Ejection Fraction," by Susheel, K. Kodali et al.; University of California, San Francisco, San Francisco, CA; American College of Cardiology; Abstract; Control/Tracking No. 04-A-298236-ACC; printed on Sep. 17, 2003; 2 pgs.

"Two-Dimensional Echocardiographic Phase Analysis—Its Potential for Noninvasive Localization of Accessory Pathways in Pateients With Wolff-Parkinson-White Syndrome," by Helmut F. Kuecherer, et al.; Circulation vol. 85, No. 1; dated Jan. 1992; pp. 130-142.

"Improvement in Echocardiographic Evaluation of Left Ventricular Wall Motion Using Still-Frame Parametric Imaging," by Enrico G. Caiani, et al.; Journal of the American Society of Echocardiography; dated Sep. 2002; vol. 15, No. 9, pp. 926-934.

"Clinical Applications of Strain Rate Imaging," by Gabriel Yip MD et al.; Journal of the American Society of Echocardiography; Dec. 2003; pp. 1334-1342.

"Colour Encoded Endocardinal Tracking: The Current State of Play," by D.G. Platts and M.J. Monaghan, Cardiology Department, King's College Hospital, London, U.K.; 2002 The European Society of Cardiology; Eur J. Echocardiography, vol. 4, Issue 1, Mar. 2003; pp. 6-16.

"Quantitation of Basal Dyssynchrony and Acute Resynchronization from Left of Biventricular Pacing by Novel Echo-Contrast Variability Imaging," by Miho Kawaguchi, MD et al.; Journal of the American College of Cardiology, vol. 39, No. 12, 2002; pp. 2052-2058.

* cited by examiner

MOTION ANALYSIS IMPROVEMENTS FOR MEDICAL DIAGNOSTIC ULTRASOUND

REFERENCE TO RELATED APPLICATIONS

The present patent document claims the benefit of the filing date under 35 U.S.C. §119(e) of Provisional U.S. Patent Application Ser. No. 60/542,121, filed Feb. 5, 2004, which is hereby incorporated by reference.

BACKGROUND

The present invention relates to analysis of motion. In particular, medical diagnostic ultrasound data is used to analyze tissue motion.

Intrinsic patient involuntary movements cause motion of tissue and blood in ultrasound images. In the cardiovascular systems, blood, cardiac, vessel or other movements determine abnormal and normal clinical states. Medical diagnostic ultrasound imaging is used to assist in diagnosis. For example, breathing, cardiac pulsations, arterial pulsations and muscle spasms are imaged. The heart rate may be used in conjunction with imaging for visual assessment of cardiac motion. The visual assessment identifies abnormal operation and wall thickening. For muscular skeletal examinations, joint and ligament motions may provide diagnostic information.

Doppler tissue imaging, strain rate imaging, M-mode imaging, examination of a sequence of B-mode images, or detecting the outline or borders of chambers of a heart following myocardial wall motion are used to diagnose cardiac motion. These various modes of ultrasound imaging maybe time-consuming or difficult. For example, tissue Doppler imaging is angle dependent, and strain or strain rate imaging is time-consuming. As another example, boundary detection is sensitive to ultrasound speckle noise. In addition, those methods provide no direct motion timing assessment.

Cardiac resynchrony therapy is used to restore heart function, but may have a limited success, such as 60-70%. The unsuccessful cases are either not improved or worsened. Since cardiac resynchrony therapy is a high cost operation with some risks, it is desirable to prescreen the patients before the operation. The location and timing of a pacemaker is desirably optimized during the operation. Follow-up examination is also desired. Imaging may assist this or other therapies.

Phase and/or amplitude analysis of ultrasound data provide parametric imaging, such as disclosed in U.S. Publication No. 2005/0107704, published May 19, 2005, (U.S. application Ser. No. 10/713,453), the disclosure of which is incorporated herein by reference. A sequence of images is analyzed to determine the onset time of periodical motion as well as the amplitude of the motion. Pixel intensity changes in two-dimensional image sequences are analyzed with the Fournier transform. The relative phase of the first harmonic to the heart cycle identifies the onset time of motion, and the amplitude represents the motion magnitude. A series of images with isolated phase information are then generated. The phase intervals for the isolated phase information shift as a function of time within the cardiac cycle. As a result, the contractions of the heart are visually highlighted in a same way but for different phases throughout the heart cycle. Amplitude analysis may be used to generate images with reduced speckle content or to better detect borders.

BRIEF SUMMARY

By way of introduction, the preferred embodiments described below include methods and systems for medical imaging with motion analysis. The phase or associated amplitude analysis of a sequence of images is improved by, first, providing a quantification. For example, a value or values representing asynchrony between different locations through a sequence of images may provide useful diagnostic information. Second, since heart motion or other motion within a body may be complex, multiple harmonics may be used for parametrically imaging a motion with phase or amplitude analysis. The multiple harmonic information may be used to identify a region of maximum motion, such as peak velocity or contraction. The maximal information may indicate the relative time of motion between different regions within an imaging sequence. Third, where different portions of a cycle have different characteristics, such as the systolic and diastolic phases of a heart cycle, images associated with each of the portions may be separated from other portions. A phase or amplitude analysis of the sequence of images for each portion is performed separately. The three improvements discussed in the paragraph above may be used individually or in any possible combination.

In a first aspect, a method is provided for medical imaging with motion analysis. First and second phases of cyclically varying imaging values relative to a cycle for first and second spatial locations, respectively, are identified. A quantity is determined as a function of the first and second phases.

In a second aspect, a computer-readable storage medium is provided. The storage medium has stored therein data representing instructions executable by a programmed processor for medical imaging with motion analysis. The instructions are for identifying phases of cyclically varying imaging values relative to a cycle for different spatial locations. A quantity is determined as a function of the phases.

In a third aspect, a method is provided for medical imaging with motion analysis. A phase of a cyclically varying imaging value is identified relative to a cycle for a spatial location. The phase information is derived from two or more harmonic frequencies and excludes other frequency components. A time-intensity curve is generated as a function of time versus intensity which includes the information at two or more harmonic frequencies of the original sampled data. A substantial maximum of a derivative or of intensity on the time-intensity curve is identified. Information is displayed as a function of a time to the substantial maximum for the spatial location.

In a fourth aspect, a method is provided for medical imaging with motion analysis. Imaged data from a first portion of a cycle is separated from imaged data from a second portion of the cycle. Two phases of a cyclically varying imaging value are identified relative to the first portion of the cycle, one for the first portion and the other for the second portion. Information is generated as a function of the phases. Alternatively, a single portion and phase are used.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
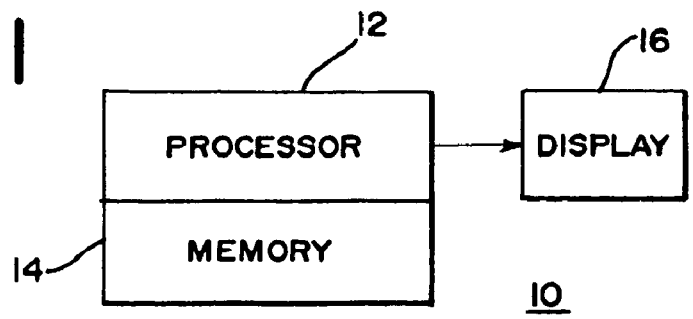
FIG. 1 is a block diagram of one embodiment of a system for medical imaging with motion analysis.

Applying a Fournier transform or otherwise analyzing intensity variation in a cyclical pattern through a sequence of images may be improved through quantification, inclusion of multiple harmonics and/or isolation of information associated with only a portion of one or more cycles. Phase analysis allows identification of the onset time of periodical motion as well as an amplitude of the motion. Determining a quantity associated with the analysis, such as identifying differences between different spatial locations, may assist in diagnosis. The differences allow analysis of motion asynchrony (i.e., desynchrony). For example, the asynchrony between the septum and lateral wall is determined from cycle phase information. In one experiment, sequences of images associated with a left bundle branch block had a mean and standard deviation of absolute asynchrony of 182±142; sequence of images associated with diseased hearts with narrow QRS and normal ejection fractions had a mean and standard deviation of 85±68; and a sequence of images associated with athletes had a mean and standard deviation of 56±46 milliseconds. Calculating the mean and/or standard deviation of asynchrony between the septum and lateral wall in an apical four chamber view may indicate a significant timing difference, indicating left bundle branch blockage. The same or different quantifications may be used for indicating other conditions.

Cardiac motion includes systolic and diastolic phases. Analyzing cyclically variations separately for each of these two different phases may provide useful diagnostic information, such as highlighting the myocardium region or isolating different operation of the heart. Motion irregularity may be more likely revealed in separately analyzed portions. Other divisions of the heart cycle or divisions of other types of cycles, such as the respiratory cycle, may be used.

Cardiac and other motions include complex patterns, such as twisting, squeezing and contraction. Given ultrasound imaging speckle noise and motion complexity, phase analysis using multiple harmonics, such as the fundamental and at least one additional other harmonic, may identify information for diagnosis. By analyzing cyclical variation using multiple frequency bands, a maximum deviation or intensity may be used to identify a time to peak contraction or other motion characteristic. The time-to-peak velocity is estimated as the time to a maximal grayscale change, and the time-to-peak contraction may be estimated as the time to a maximal grayscale amplitude. The maximum identifies the time-to-peak velocity or contraction for two-dimensional imaging or quantification.

The aspects in the above three paragraphs may be used individually or in combination. For example, separate analysis for different portions of cycles and use of two or more frequency bands in the analysis may be used individually or in combination for generating multi-dimensional images without determination of a quantity. Alternatively or additionally, a quantity is calculated. These aspects may be used for diagnosis or imaging of the heart or other structure.

FIG. 1 shows a system 10 for motion analysis in medical imaging. In one embodiment, the system 10 is a medical diagnostic ultrasound system, but other medical systems may be used, such as magnetic resonance, positron emission, computed tomography or x-ray imaging. The system 10 is a system for scanning, a workstation or personal computer.

The system 10 includes a processor 12, a memory 14 and a display 16. Additional, different or fewer components may be provided. The processor 12 is a general processor, control processor, application-specific integrated circuit, field-programmable gate array, digital circuit, analog circuit, digital signal processor, combinations thereof, or other now known or later developed devices for performing motion analysis. The memory 14 is a cache, buffer, RAM, removable media, hard drive or other computer-readable storage media. Computer-readable storage media include various types of volatile and non-volatile storage media. The functions, acts or tasks illustrated in the figures or described herein are performed by the processor 12 executing instructions stored in or on the computer-readable storage media of the memory 14. The functions, acts or tasks are independent of the particular type of instructions set, storage media, processor or processing strategy and may be performed by software, hardware, integrated circuits, filmware, microcode and the like, operating alone or in combination. Likewise, processing strategies may include multi-processing, multi-tasking, parallel processing and the like. In one embodiment, the instructions are stored on a removable media device for reading by a medical diagnostic imaging system. The imaging system uploads the instructions for performing the acts discussed herein. In another embodiment, the instructions are stored in a remote location for transfer through a computer network or over telephone lines to an imaging system or workstation. In yet other embodiments, the instructions are stored within the imaging system or workstation.

The processor 12 receives a sequence of medical images. For example, a previously acquired sequence of medical images are stored in the memory 14 or transferred from a remote location. As another example, a sequence of images is acquired in real time, and the processor 12 performs motion analysis as the images of a sequence are acquired. The sequence of images is associated with one or more indicators of time, such as a time stamp for each set or frame of data, an indication of time relative to a cycle, or an indication of an ECG or other sensor output at the time of acquisition. Alternatively, a sensor input or other time indicator is input to the processor 12 separate from the imaging sequence. In yet another embodiment, the processor 12 is operable to analyze the image data to determine the timing or cycle information, such as identifying a cyclical flow using Doppler data.

Each image in the sequence represents a two- or three-dimensional region. Image as used herein includes data representing spatial locations prior to display or actual displayed values. A frame of data for two-dimensional imaging includes information for a plurality of different spatial locations along a plane. Data representing a three-dimensional region includes information representing different spatial locations along three dimensions in a volume. The data representing each spatial location includes an intensity, such as a B-mode value. Alternatively, the intensity values include Doppler velocity, variance or power values. Other amplitude, magnitudes, energies or powers may be used as intensities.

Figure 2:
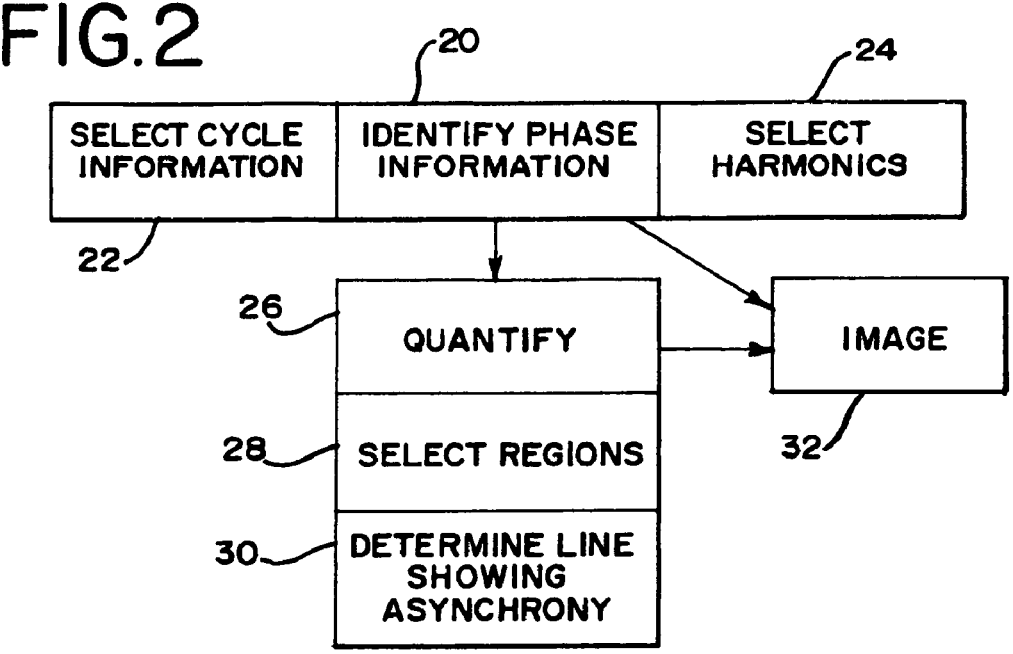
FIG. 2 is a flowchart diagram of one embodiment of a method for medical imaging with motion analysis.

FIG. 2 shows a method for medical imaging with motion analysis. The method is implemented on the system 10 of FIG. 1 or a different system. Additional, different or fewer acts may be provided. For example, acts 20 and 26 are provided without acts 22, 24 or 32. As another example, acts 20 and 32 are provided without act 26.

In act 20, phase and amplitude information are identified from the sequence of images. For a given spatial location throughout the sequence of images, the imaging value may vary relative to a cycle. For example, as the heart contracts and expands in an apical four chamber or other view, intensity values may vary. The phase of the variation relative to the heart cycle is identified. Different spatial locations may be associated with variation that occurs at different portions within the heart cycle. The phase analysis is performed for one or more spatial locations. In one embodiment, the motion analysis and/or imaging disclosed in U.S. Publication No. 2005/0107704, published May 19, 2005 (U.S. application Ser. No. 10/713,453), the disclosure of which is incorporated herein by reference, is used.

Figure 3:
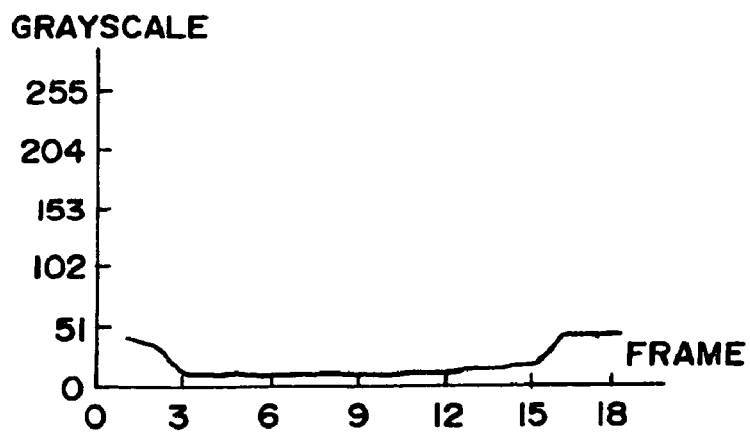
FIG. 3 is a graphical representation of an intensity value as a function of time or frame throughout a cycle.

FIG. 3 shows an example of a change in pixel intensity at a given pixel location near the edge of the left atrium of the myocardium in an apical four chamber clip for a single cycle from an R-wave to a subsequent R-wave. As shown, eighteen frames of data are acquired through the cycle, providing eighteen samples of the intensity at the given location. Other numbers of frames may be used. Other spatial locations associated with moving structures, such as the myocardium, may have similar variations, but with different phasing or amplitude. Spatial locations associated with no movement, such as blood pools or stationary tissue, are masked, ignored or included in the analysis. FIG. 3 shows the pixel intensity change as similar to a sinusoid curve given as: $Y=COS(\omega t+\theta)$ where $\omega$ is the angle speed, $\theta$ is the phase term, t is the time, and Y is the resulting value.

Figure 4:
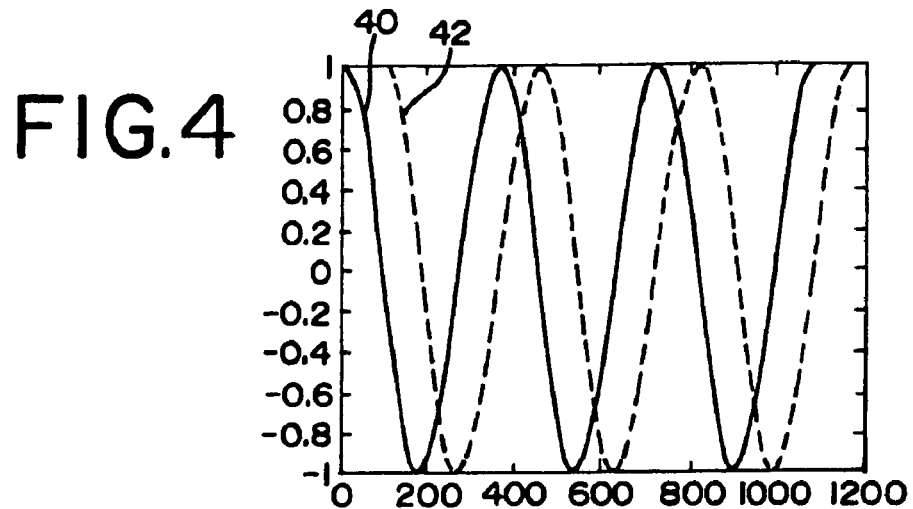
FIG. 4 is a graphical representation of phase analysis of a first harmonic of the intensity shown in FIG. 3.

The motion represented by the sequence of images is analyzed as a function the cyclically varying image values shown in FIG. 3 and other values for other spatial locations. In one embodiment, the cyclical varying image values are transformed into a frequency domain using a Fournier transform. Other transformations or analysis in the time-domain may alternatively be provided. The relative phase of the transformed values for a given spatial location is determined with respect to the cycle. FIG. 4 shows a sinusoid 40 matched to a given heart cycle. Alternatively, more complex cycle information than a single sinusoid 40 is provided. The first harmonic or fundamental information of the varying pixel value shown in FIG. 3 provides the sinusoid 42 shown in FIG. 4. The sinusoid 42 indicates a 90° phase shift from the heart cycle sinusoid 40. Accordingly, the onset of motion associated with the identified spatial location occurs with a phase shift of 90° behind the onset of the cardiac cycle. The same or other spatial locations may have more, less or the same phase shift.

The onset time of motion may be represented by the phase of the sinusoidal curves. The phase shift whose absolute value is between zero and 360° may be converted into a change in time or delay from a given heart or other cycle marker, such as the R-wave. The change in time is represented by: $\Delta t=60,000\Delta\theta/360b$ where $\Delta t$ is the delta time in milliseconds, $\Delta\theta$ is the phase shift and b is the heart rate. The heart rate is determined from ECG input, ultrasound data processing, identification of valve opening and closing times, user input or other sources. The relative amplitude based on the transformed information at a desired frequency or frequency band may additionally be calculated.

The phase and/or amplitude information is identified for a plurality of spatial locations. For example, phase and amplitude information are determined for each of a plurality of spatial locations for two- or three-dimensional images within a sequence. As another example, phase and amplitude information are identified for spatial locations associated with moving tissue of interest, such as a myocardial wall, a septum, a lateral wall, ventricle wall, blood vessel, or other moving tissue of interest. Locations for analysis are identified using a manual user input, automatically using algorithms, or a combination of manual input and algorithms. For example, a user indicates one or more locations along a boundary of interest and the processor automatically determines an associated boundary using gradient, pixel intensity or other information. In another embodiment for identifying a mask or tissue regions of interest, the amplitudes at the given frequency or frequencies of interest of the imaging values for the spatial locations within a sequence of images are identified in the frequency domain. Amplitudes that exceed a given threshold indicate spatial locations that undergo significant change or show motion within the sequence. Spatial locations showing insignificant change are masked out in further phase analysis. Low-pass filtering or other algorithms may be applied to provide more contiguous regions for inclusion or exclusion in the mask.

In act 32, an image is generated as a function of the identified phase and/or amplitude information. For example, the sequence of B-mode images are color modulated where different colors represent the different phases. A single image may be provided to show relative phase shifts throughout the sequence. Alternatively or additionally, the sequence of images is color modulated where different relative phases are highlighted in the sequence of images at different times throughout the cycle. Similarly, the amplitude information identified through the Fournier transform is used to generate an image or modulate a sequence of images. In the experiment, the septum and the lateral wall in the normal cases were moving in synch and out of synch with the atrium, while in the LBBB cases, the septum was in synch with the atrium and out of synch with the lateral wall. In a static image derived from the phase information for each spatial location, color coding shows the differences in synchronization.

In act 24, the identification of phase and/or amplitude information of act 20 is set or altered as a function of the desired frequency bands of interest in the frequency-domain. For example, fundamental or first harmonic information is selected for phase analysis. Information at other frequencies is removed or reduced. As another example, information at two or more harmonic frequencies, such as the first, second and third harmonic frequencies is identified and used for phase analysis and information at other frequencies, is excluded or limited. The relative phase or onset time is calculated from the information at the selected frequencies of interest.

In other embodiments, the information at two or more frequencies identified in the frequency-domain may be used for generating an image or quantity in the time-domain. Time-intensity curves for one or more spatial locations are generated as a function of the phase information associated with the multiple frequencies. Since the motion may include complex patterns, the reconstructed time-intensity curve for each spatial location may accurately represent the motion while removing undesired frequency information.

The time-intensity curve is analyzed to identify information of interest. Any characteristic of the time-intensity curve may be identified. For example, the time or frame index associated with the substantial maximum brightness or intensity is identified. The frame index or time associated with the maximum intensity provides a time-to-peak contraction. As another example, the time or frame index associated with the substantial maximum of a first derivative of the time-intensity curve is identified. The frame index or time associated with the maximum of the first derivative may provide a time-to-peak velocity. The times are set relative to the heartbeat or other cycle. If multiple similar or same maximum brightness or derivatives exist, the first occurrence is used. Alternatively, other occurrences are identified.

The frame index or time information is used to color code one or more images as discussed above for act 32. For example, a static image is generated where each pixel value represents a time-to-peak velocity or a contraction. The image may include color and brightness encoding to separately indicate time-to-peak velocity and time-to-peak contraction. The sequence of images may be color encoded to highlight locations of different phases in different images. As an alternative or at addition to generating an image, the time information is used as discussed herein for calculating a quantity, such as a level of asynchrony.

In act 22, the identification of phase and amplitude information of act 20 is performed separately for different portions of a cycle. Information associated with a subset of a cycle or the same subset portions of multiple cycles is selected for identification of phase information relative to the cycle. For example, frames of data or other data between end diastole and end systole is separated from data between end systole and end diastole (i.e., systolic phase data and diastolic phase data). Where information from multiple cycles existed in the sequence, information from a single cycle is separated or selected or information from the same portion and different cycles is combined. By separating the information, irregular heart function may more likely be identified. The data from the different selected portions is then analyzed for motion, such as to identify an onset time of motion relative to a heart cycle or a pseudo cycle derived from the selected portion.

Since the phase and amplitude motion analysis performed in act 20 is relative to a cycle, the selected sequence of frames of data is mirrored, interpolated, extrapolated or otherwise used to form data representing a complete cycle based on the selected portion. Where the selected portion is greater than or less than a half of the full cycle, the cycle used for comparison is altered to correspond to the newly formed data from the selected portion. For example, the systolic phase is of a different length than the diastolic phase. The contraction time period for the heart is smaller than the relaxation time period. A Fournier analysis is performed to identify a phase and/or amplitude information for the selected portion. A phase of a cyclically varying image value relative to the derived pseudo cycle is identified. Spatial locations associated with motion during the selected portion may be isolated. For example, amplitude information from the Fournier analysis is used to create a mask.

Information is generated as a function of the phase and/or amplitude information determined for a single spatial location or multiple spatial locations, from the selected portions of a cycle. For example, a quantity is calculated as discussed above for one or more spatial locations or regions using the phase or timing data of the selected portion. Using data from different portions of a cycle, mechanical disynchrony information is generated about the myocardium or other tissue in different phases, such as systolic and distolic phase. As another example, an image is modulated as a function of the phase and/or amplitude information derived from the selected portion. Where data of a selected portion is mirrored to provide a full cycle, the resulting phase information may be binary, such as zero or 180° out of phase. Generating an image or providing quantities based on binary phase information of a fundamental harmonic indicates either synchronized or asynchronous operation, more easily identifying asynchronous behavior for a medical practitioner.

In act 26, a quantity is determined as a function of phase or amplitude information identified in act 20. Any of various quantities now known or later developed may be calculated from the phase or amplitude information. For example, phase information from different spatial locations or different regions is used to show an amount of synchrony or asynchrony between the different locations. The difference in phase indicates a level of asynchrony. For example, the average phase of a selected region is compared to the average phase of a different selected region. The difference between the average phases or times of onset of motion indicates the level of asynchrony. Synchronous motion is provided where little time difference in the onset of motion occurs.

Figure 5:
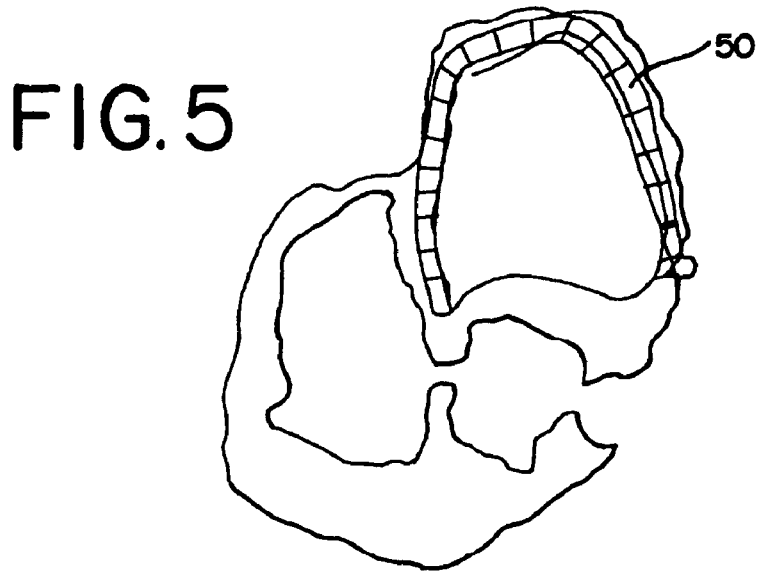
FIG. 5 is a graphical representation showing segmentation of a myocardial wall in one embodiment.

The quantity indicating the level of synchrony may be determined as a function of more than two regions. For example and as shown in FIG. 5, an identified region of moving tissue is segmented in act 28. FIG. 5 shows twenty segments 50 formed along a left ventricle of the indo-boundary from the basil point of the septum to the basil of the lateral wall. More or fewer segments 50 may be provided in a full sampling or sparse sampling. Different walls, tissue structures or other regions may be identified. The segments 50 are established by manual indication, automatically or semi-automatically. For example, the user indicates a beginning point, an end point and a point between the two. The system then automatically tracks a boundary associated with the three points and then equally divides the boundary. An identified width or a standard width, such as 4 mm, for the segmentation may be provided. While shown as an open loop in FIG. 5, the segmentation may be provided in a close loop. The phase information for each of the segments 50 is calculated after segmentation or is selected where calculated before segmentation.

Figure 6:
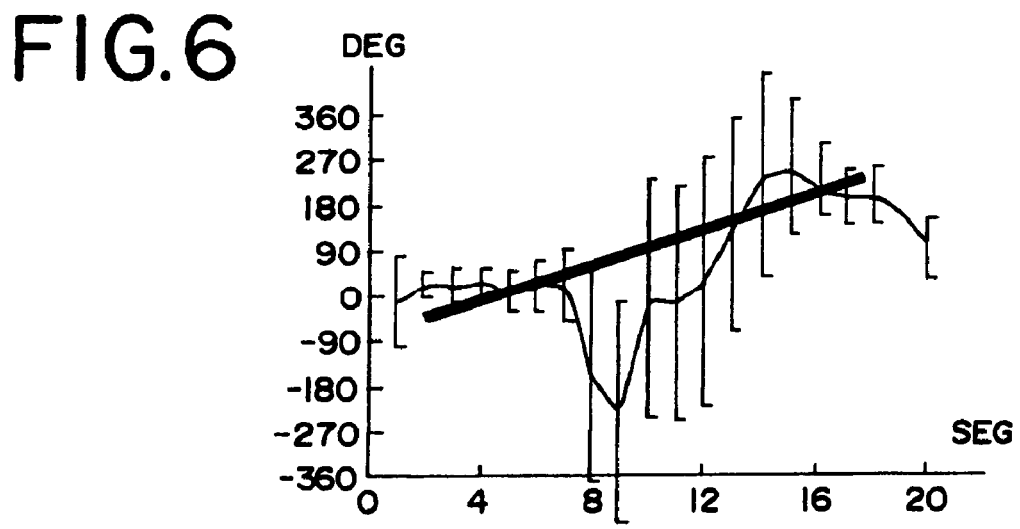
FIG. 6 is a graphical representation of one embodiment of quantification of asynchrony.

The mean, variance or other quantity of the phase and/or amplitude information for each tissue region or segment 50 is determined. Where multiple phases are determined within a same tissue region, the average or weighted average is calculated for the region. In one embodiment, the quantities associated with each segment 50 are displayed as numerical values or a graph as shown in FIG. 6.

In act 30, a quantity that is a function of three or more segments 50 is calculated from the mean, variance (e.g., standard deviation) or both mean and variance information for the segments 50. For example, a line is determined as a function of the mean and variance of phase information for a plurality of the segments 50. The onset time of the septum relative to the lateral wall may provide useful asynchrony information. The segments are sequentially labeled where the first segment 50 is at the basil point of the septum. Septum segments 2-6 and the lateral wall segments 15-19 are used to fit a linear line. As shown in FIG. 6, the means of the phase for segments 2-6 and 15-19 as well as the associated variance are plotted and are used to identify a line, such as through linear regression where greater variance may indicate a lesser weighting of the associated mean. The phase information for segments 1, 7-14 and 20 is ignored. Different segments 50, such as all the segments 50 or different subsets of the segments 50 may be used for determining the quantity. The asynchrony is provided in terms of a time difference between the septum and lateral wall motion represented by the line. The time difference or asynchrony quantity is provided by:

$$\Delta t = \frac{(14-7+1)a}{360} \times \frac{60000}{b} \quad 5$$

where a is the slope of the fit line and b is the heart rate. The calculated time difference, the slope, the line, the graph shown in FIG. 6 showing a mean and variance with or without the line or other quantities are displayed. The phase shift between the two opposite walls is computed as the slope of the straight line times the segment gap between the two walls, such as the gap between segments 14 and 7 inclusive. The heart rate portion of equation 3 converts the phase shift information to a time difference. Either a time difference or a phase shift may be used.

To avoid noise information, the quantity may be determined free of information from spatial locations not associated with tissue movement, such as using amplitude thresholding to mask the data. The quantity is determined from information of some spatial locations and not from information of other spatial locations.

As represented by the mean and variance of the asynchrony levels discussed above for three different groups in an experimental study, the asynchrony level may be compared to a threshold for identifying areas of concern or diagnosing heart or other tissue performance. A level of asynchrony may correlate with a level of ejection fraction. For example, where the level of asynchrony is 150 milliseconds or greater, a left bundle branch block may be indicated. Different experimental results may indicate different thresholds for the same conditions or different conditions. Additionally, experimentation may indicate other quantities associated with the phase or amplitude information of the cyclically varying imaging values relative to the cycle useful for identifying particular conditions.

While discussed above for apical four chamber view, a short axis, two chamber or other views may be used. The level of asynchrony, a location associated with the greatest or least amount of asynchrony, an image showing different relative phases or other information may be used for cardiac resynchronization therapy. For example, experimentation may show that proper placement for a cardiac pacemaker may be indicated using the phase information or a quantity calculated from the phase information.

As shown in FIG. 6, the standard deviation of segments 50 at the apex region, such as segments 7-14, is large. To reduce variance within the phase estimation, information from multiple cycles may be averaged before calculation of phase or the resulting phase information from different cycles may be averaged. Use of high frequency probes and general best practices for acquiring the imaging sequence may further reduce variance. The phase analysis is not scan angle dependent, but may be altered due to motion of a transducer. By using respiratory gating or triggering, having a patient hold their breath or other standard scan techniques, transducer motion may be limited. The combination of phase information and amplitude information may be used to further distinguish conditions. Different quantities calculated from phase or amplitude for one or more spatial locations may indicate different conditions.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for medical imaging with motion analysis, the method comprising:
    obtaining a sequence of frames of data representing a region at different times, the region including a plurality of different spatial locations;
    identifying from a sequence of frames using a processor, first and second phases of sinusoids representing cyclically varying imaging values over time for first and second spatial locations, respectively, the phases being of an offset of the sinusoids relative to a wave representing a physiological cycle, each of the first and second locations being in each scan of a plurality of scans, the imaging values from each of the first and second locations being used separately for the identifying, the first and second phases being phase differences of the sinusoids of the variations of the imaging values over time with the physiological cycle, the phase differences comprising an amount of the offset, wherein the identifying is performed for a plurality of spatial locations including the first and second spatial locations and other spatial locations in at least three segment regions;
    determining a quantity as a function of the first and second phases;
    and displaying, on a display, an image as a function of the quantity, the image having a phase axis and a location axis, a curve of the first, second and other phases as a function of the first, second, and other spatial locations, a straight line fit to the first, second, and other phases, and an indication of variance for each of the first, second, and other phases.

2. The method of claim 1 wherein determining the quantity comprises determining an asynchrony level between the first and second spatial locations as a function of the first and second phases.

3. The method of claim 2 wherein determining the asynchrony comprises determining a timing difference as a function of the first and second phases.

4. The method of claim 1 wherein identifying comprises:
    transforming the cyclically varying imaging values into a frequency domain;
    identifying the first and second phases as a function of phase shifts of at least one frequency term of the cyclically varying imaging values from the cycle.

5. The method of claim 1 wherein the plurality of spatial locations representing a two- or three-dimensional region, the identifying being a function of a plurality of images, each of the plurality of images corresponding to one imaging value for each spatial location of the cyclically varying imaging values.

6. The method of claim 5 further comprising:
    identifying amplitudes of the cyclically varying imaging values for the other spatial locations at a frequency of interest in a frequency domain; and
    masking out some of the other spatial locations as a function of the amplitudes;
    wherein determining the quantity comprises determining the quantity free of information from the masked out some of the other spatial locations.

7. The method of claim 1 wherein the plurality of spatial locations representing a two- or three-dimensional region;
    further comprising:

selecting a plurality of tissue regions as the segment regions, the first spatial location in a first one of the plurality of tissue regions and the second spatial location in a second one of the plurality of tissue regions, the first phase being a function of the first tissue region and the second phase being a function of the second tissue region; and wherein determining a quantity comprises calculating a mean, a variance or combinations thereof of the first and second phases.

8. The method of claim 1 wherein determining the quantity comprises determining an asynchrony as a function of the first and second phases; and further comprising:

comparing the asynchrony to a threshold.

9. The method of claim 1 wherein identifying comprises identifying for first and second spatial locations at a septum and lateral wall, respectively, on a ventricle wall of a heart.

10. The method of claim 1 wherein identifying comprises identifying the first and second phases with information at two or more harmonic frequencies.

11. The method of claim 10 further comprising:

generating first and second time-intensity curves for the first and second spatial locations as a function of the first and second phases with information at two or more harmonic frequencies, respectively;

identifying a first and second maximum of a first derivative or of intensity of the first and second time-intensity curves, respectively; and displaying an image as a function of a time to the first and second maximum for the first and second spatial locations.

12. The method of claim 1 wherein identifying and determining the quantity are performed separately for at least two different portions of a cycle.

13. A non-transitory computer readable storage medium having stored therein data representing instructions executable by a programmed processor for medical imaging with motion analysis, the storage medium comprising instructions for:

obtaining a sequence of frames of data representing a region at different times, the region including a plurality of different spatial locations;

identifying from a sequence of frames first and second phases of sinusoids representing cyclically varying imaging values over time for first and second spatial locations, respectively, the phases being of an offset of the sinusoids relative to a physiological cycle, the first and second spatial locations being separate locations in each of a plurality of scans, the first and second phases being separate phase differences of the sinusoids of the variation of the imaging values over time with the physiological cycle, the phase differences comprising an amount of the offset;

determining a quantity as a function of the first and second phases;

and displaying an image having a phase axis and a location axis, a curve including the first and second phases as a function of the first and second spatial locations, a line fit to the first and second phases, and an indication of variance for the first and second phases.

14. The storage medium of claim 13 wherein determining the quantity comprises determining an asynchrony level between the first and second spatial locations as a function of the first and second phases.

15. The storage medium of claim 13 wherein identifying comprises:

transforming the cyclically varying imaging values into a frequency domain;

identifying the first and second phases as a function of phase shifts of at least one frequency term of the cyclically varying imaging values from the cycle;

wherein identifying is performed for a plurality of spatial locations including the first and second spatial locations and other spatial locations, the plurality of spatial locations representing a two- or three-dimensional region; and further comprising:

selecting a plurality of tissue regions, the first spatial location in a first one of the plurality of tissue regions and the second spatial location in a second one of the plurality of tissue regions, the first phase being a function of the first tissue region and the second phase being a function of the second tissue region; and wherein determining a quantity comprises calculating a mean, a variance or combinations thereof of the first and second phases.

16. The storage medium of claim 13 wherein determining the quantity comprises determining the line as a function of the first and second phases.

17. A method for medical imaging with motion analysis, the method comprising:

obtaining a sequence of frames of data representing a region at different times, the region including a plurality of different spatial locations;

for a first of the different spatial locations, identifying a first periodic change over time of the data, the data representing the first spatial location in the frames of the sequence;

for a second of the different spatial locations, identifying a second periodic change over time of the data, the data representing the second spatial location in the frames of the sequence;

obtaining a physiological cycle waveform different than the first and second periodic changes;

identifying a first amount of a first phase difference of the first periodic change to the physiological cycle waveform;

identifying a second amount of a second phase difference of the second periodic change to the physiological cycle waveform;

determining a quantity as a function of the first and second phase differences; and displaying, on a display, an image as a function of the quantity, the image having a phase axis and a location axis, a curve including the first and second phases as a function of the first and second spatial locations, a straight line fit to the first and second phases, and an indication of variance for the first and second phases.

* * * * *